United States Patent [19]

Harrison

[11] Patent Number: 4,578,282

[45] Date of Patent: Mar. 25, 1986

[54] COMPOSITION FOR DIAGNOSTIC REAGENTS

[76] Inventor: James S. Harrison, 12 Sioux La., Ringwood, N.J. 07456

[21] Appl. No.: 688,975

[22] Filed: Jan. 4, 1985

Related U.S. Application Data

[62] Division of Ser. No. 345,589, Feb. 4, 1982, Pat. No. 4,493,821.

[51] Int. Cl.⁴ ............... G01N 33/545; G01N 33/552; C09Q 15/04
[52] U.S. Cl. ........................ 422/57; 252/380; 252/397; 424/3; 436/527; 436/531
[58] Field of Search ............... 422/56, 57; 424/3; 427/2; 436/518, 519, 520, 521, 527, 531, 826; 252/380, 397

[56] References Cited

U.S. PATENT DOCUMENTS

| | | | |
|---|---|---|---|
| 2,092,566 | 9/1937 | Wright | 23/253 |
| 2,554,944 | 5/1951 | Ferrari | 8/94.11 |
| 2,770,572 | 11/1956 | Eldon | 167/84.5 |
| 3,074,853 | 1/1963 | Brewer | 167/84.5 |
| 3,088,875 | 5/1963 | Fisk | 167/84.5 |
| 3,171,783 | 3/1965 | Fisk | 167/84.5 |
| 3,234,096 | 2/1966 | Pollack | 167/84.5 |
| 3,236,732 | 2/1966 | Arquilla | 167/84.5 |
| 3,309,275 | 3/1967 | Treacy | 167/84.5 |
| 3,415,361 | 12/1968 | Adams et al. | 206/47 |
| 3,502,437 | 3/1970 | Mass | 23/253 |
| 3,551,555 | 12/1970 | Schuurs | 424/12 |
| 3,562,384 | 2/1971 | Arquilla | 424/12 |
| 3,579,306 | 5/1971 | Crane | 23/253 |
| 3,624,197 | 11/1971 | Schain | 424/3 |
| 3,666,421 | 5/1972 | Price | 23/253 TP |
| 3,737,335 | 6/1973 | Feinberg | 117/72 |
| 3,770,383 | 11/1973 | Price | 23/253 TP |
| 3,790,663 | 2/1974 | Garrison et al. | 424/12 |
| 3,862,300 | 1/1975 | Westlake et al. | 424/3 |
| 3,966,897 | 6/1976 | Renn | 424/1.5 |
| 3,975,162 | 8/1976 | Renn | 23/253 TP |
| 4,234,316 | 11/1980 | Hevey | 23/230 |
| 4,302,480 | 11/1981 | Fischer | 427/2 |
| 4,387,164 | 6/1983 | Hevey et al. | 436/56 |

*Primary Examiner*—Arnold Turk
*Attorney, Agent, or Firm*—Bruce M. Collins

[57] ABSTRACT

A fixative composition for histological, cytological, immunological and proteinaceous preparations comprising a mixture of pyrrolid-2-one, a polyol, a urea and a zinc salt of a non-oxidizing organic or inorganic acid. Also disclosed are devices utilizing such compositions.

18 Claims, No Drawings

COMPOSITION FOR DIAGNOSTIC REAGENTS

CROSS REFERENCE

This is a divisional of Ser. No. 345,589 filed on Feb. 4, 1982, now U.S. Pat. No. 4,493,821.

DETAILED DESCRIPTION

This invention pertains to a fixative and preservative compositions for histological, cytological, immunological and proteinaceous preparations and to novel devices and test systems made possible by the unique properties of the composition.

The use of fixatives to preserve histological and cytological preparations is, of course, well known and widely practiced. Invariably these are liquid preparations which are applied to the sample or in which the sample is immersed. Lerner et al. disclose in U.S. Pat. No. 3,546,334 a cytological fixative solution of a polyalkylene glycol, water, a C-1 to C-10 alcohol and a ketone which is sprayed on to a slide on which has been previously placed a smear of body cells. According to the disclosure, alcohol, water and ketone evaporate leaving a protective film of the polyethylene glycol over the smear.

Westlake et al. in U.S. Pat. No. 3,997,656 describe a histological staining method in which tissue is first immersed in an aqueous fixing solution of trichloroacetic acid, zinc chloride and formaldehyde. A wax such as polyethylene glycol can be included in the fixing solution as a lubricant and sealant.

Ehrenreich, in U.S. Pat. No. 3,389,052 enumerates various approaches to fixing cytological smears, all of which involve the application of a liquid fixative, often ethanol and ethyl ether. This reference also describes the use of an improved composition in aerosol form of a lower alkanol, a mixture of a liquid and a solid polyethylene glycol and propellant which is sprayed on the smear.

The present invention is a departure from these approaches in that it provides a fixative which is preapplied to a slide or other test surface and which presents a substantially dry, non-fluid surface to which the sample is applied. Mere contact between the surface and the sample effects fixing and preservation so that only the act of transferring the sample to the test surface is required. The sample need not be disturbed as in the past by the separate application of fixative.

The advantages flowing from this development are numerous. Firstly, precoated slides can be provided to individual practitioners. Cytological smears then can be directly applied. The slide can be subjected to such diagnostic tests as indicated or maintained for subsequent testing, without the need for additional fixing or preservative operations.

In addition, there is no need to adhere to a rigid fixing protocol, as is often the case with liquid or spray fixatives. As a result, one can achieve greater uniformity of results, the pre-application of the fixative material being admirably suited to standardization.

Moreover, because of the essentially "dry" nature of the preparation and the special advantages attendant to the use of plastic slides, it is possible to send slides inexpensively through the mail. This not only greatly simplifies clinical screening but opens the opportunity for centralized microscopic examination for practitioners who are widely separated geographically.

The fixative and preservative properties of the composition also permits the preparation of diagnostic devices utilizing unstable biological entities such as antigens and some antibodies.

Other advantages and objects of the invention will be apparent from the following disclosure.

The basic composition comprises as its principal fixative and preservative component a four component mixture of pyrrolid-2-one, a polyol, at least one urea and a zinc salt of a non-oxidizing organic or inorganic acid. Within this mixture, the relative proportions of the four components can vary widely within certain broad ranges depending upon the specific use for which the overall composition is intended. Generally the pyrrolid-2-one will comprise from about 10% to about 75% by weight of the mixture, the polyol will comprise from about 10% to about 50% by weight of the mixture, the urea will comprise from about 1% to about 20% by weight of the mixture and the zinc salt will comprise from about 1 to about 10% by weight of the mixture. The actual relative percentages will be selected from within the respective ranges so that their sum is 100% of the mixture.

The polyol is typically a polyalkylene glycol such as polyethylene glycol or polypropylene glycol although other polyols such as glycerin can be use. One polyol which has proven to be most satisfactory is polyethylene glycol of a molecular weight of about 200.

The zinc salt can be of any non-oxidizing acid including strong inorganic acids such as hydrochloric acid (i.e., zinc chloride) or weaker organic acids such as acetic acid (i.e. zinc acetate).

Without wishing to be bound by any theory, it appears that compositions utilizing the foregoing mixture do not operate by a dehydration principle. This is to be contrasted with previous fixative compositions utilizing such materials as formaldehyde and alcohols. Rather the mixture appears to "tie up" water molecules within the cell or material, maintaining both cellular and immunological characteristics.

As will be seen supra, the mixture can be presented in different compositional embodiments. For example, the mixture ingredients may be in the form of an aqueous solution. Depending upon the strength (concentration), such solutions can be utilized as fixative preparations per se or as stock solutions for the preparation of precoated slides. For example, a 0.005% aqueous solution of a mixture of about 40 to 45% pyrrolid-2-one, about 40 to 45% polyethylene glycol, about 9 to 10% urea and about 4 to 5% zinc acetate is a suitable preservative for UCG antigen carried on milk latex. Alternatively, a solution of the same mixture can be applied to a slide and allowed to dry, thereby presenting a fixative surface.

In addition to the foregoing components of the mixture, various other components can also be present. The presence or absence of such ingredients will depend upon the the specific application. For example, immunological and proteinaceous preparations are often advantageously included on a carrier such as milk latex, coconut charcoal and the like. When these are to be combined with the basic mixture, it is desirable to include one or more colloid protective agents such, as for example, a polysaccharide derivative such as dextrin, carrageenan or an epihydrin cross-linked sucrose, a polyvinyl acetate, acrylamide, a choline-cholesterol preparation or the like. Moreover in such colloidal preparations, the addition of a small amount of a surfactant such as the alkylaryl polyether alcohols, sulfonates and the like also often can be advantageous.

In instances where a greater degree of complexing fixation is desired for tissue and other proteinaceous preparations, the addition of a small amount up to about 1% of a dialdehyde, such as glyoxal or glutaraldehyde is effective. Similarly other complexing agents, such as trichloroacetic acid can be added. Typically when present, trichloracetic acid is utilized in an amount corresponding to from about 10 to about 15% by total weight of the above-defined four component mixture.

For precoated slides it is often also desirable for adhesion of the fixed specimen to add a quantity of a film forming adjuvant such a polyvinyl alcohol, methyl ethyl cellulose, collagen or the like to the formulation. This can range from about 10% to about 20% by total weight of the above-defined four component mixture, generally added at the conclusion of other mixing operations.

In one embodiment of the present invention, a stock solution is utilized to precoat slides or other test surfaces. These will consist of a base strip of material which is non-absorbent to and insoluble in water, as for example a conventional glass microscope slide or a plastic strip or slide. Suitable for plastics include polystyrene, polyacrylate, polymethacrylate, polyethylene, polypropylene, polycarbonates, polyvinylchloride, nitrocellulose and the like. The surface will carry at least one deposition area which can extend to the entire surface or may be limited to one or more zones on the surface. Particularly in the case of plastic, the zones may be defined by suitable indentations.

On each zone is carried the evaporative residue of the particular fixative and preservative composition. Thus, a solution of the composition is applied to the surface and allowed to evaporate with gentle heating, e.g. 40° C., until sufficient liquid (predominately water) is driven off and a subtantially dry but slightly tacky residue remains. Such a precoated slide or test surface is then ready to receive a histological, cytological, immunological or proteinaceous specimen which is fixed upon application.

One particularly surprising observation involves the utilization of the present compositions with plastic surfaces where it appears the precoating tends to render the surface relatively impervious to powerful organic solvents utilized in clinical chemistry. Thus precoating a polystyrene or polymethacrylate surface as herein described results in the coated surface resisting xylene, toluene and the like.

In a further embodiment of the invention, the precoated base strip serves as a diagnostic testing device. Thus there is combined with a composition of the present invention a histological, cytological, immunological or proteinaceous diagnostic reagent system and this combination is then deposited on the base strip and dried as previously described. The reagent system includes conventional dyes and stains such as methylene blue N, cresyl violet acetate, hematoxylin, and the like, as well as counterstains such as rosaniline, magenta II, picric acid and the like (see generally U.S. Pat. Nos. 3,997,656 and 4,070,495), as well as mitocondrial dyes such as actiflavin. More significantly, the diagnostic reagent system can include materials of a biological nature which ordinarily are not amenable to prior preparation and storage. Proteinaceous substances which are reactive in diagnostic immunological reactions can be combined with the composition of the invention.

Typical of these are immunological agents such as sera, pure antibodies and antigens. While slides or test surfaces containing certain dried immunological components have been previously describe (see, e.g. U.S. Pat. No. 3,666,421), such systems have been limited to those immunological or proteinaceous materials of high stability. In addition, these systems have required a plurality of zones to prevent premature reaction, both physical and chemical, the contents of which must then be mixed in executing the particular test. Finally, such testing systems or devices lack any degree of permanence after development.

The present system provides for the preservation of, and thus permits the utilization of, otherwise unstable biological reagents such as antigens. These include antigens to antibodies and antibody-like substances as RF (arthritis), rapid plasma reagin (syphilis), IgG, IM, $\beta$-UCG and the like. Similarly antibodies including antisera and monoclonal antibodies can be incorporated in the composition and used to precoat slides or diagnostic substrate surfaces. Upon drying, the particular biological reagent is preserved but still retains its biological activity. In fact, the reagent can be preserved in a single zone even in the presence of other reactive components which are not activated until the sample is moistened, as by application of the test specimen. After completion of the test, the system can be preserved due to the remaining presence of the preserving and fixing composition, thus permitting future and comparative study.

The following examples will serve to further typify the nature of the invention but should not be construed as a limitation on the scope thereof, the invention being defined solely by the appended claims.

EXAMPLE 1

| Ingredient | Amount |
| --- | --- |
| pyrrolid-2-one | 15 g. |
| urea | 1.65 g. |
| 1,3-dimethyl urea | 1.65 g. |
| zinc acetate | 1.5 g. |
| polyethylene glycol (200 mw) | 6.25 ml. |

The ingredients are mixed with 500 ml. of distilled water and 80 g. of a 1:1 mixture Gelvatol G 40/10 and G 20/60 are added. The final solution is adjusted to pH 6.6 with aqueous sodium hydroxide. One part by weight of this preparation is combined with 9 parts by weight of charcoal/RPR antigen and 0.5 mg. of the mixture is then applied to a polystyrene slide and dried at 40° C. The single test zone is stable at room temperature and can be used in the serological detection of syphilis. RPR carbon particle antigen detects "reagin" an antibody-like substance present in sera of syphilitic persons (and occasionally in sera of persons with other acute or chronic conditions). When a specimen contains antibody, flocculation occurs with a coagglutination of the carbon particles which appears as black clumps. This coagglutination can be read macroscopically. Nonreactive specimens appear to have a light-gray color.

EXAMPLE 2

| Ingredient | Amount |
| --- | --- |
| 98% pyrrolid-2-one | 15.0 g. |
| urea | 3.5 g. |

| Ingredient | Amount |
| --- | --- |
| polyethylene glycol (200 mw) | 6.25 ml. |
| zinc acetate | 1.0 |

The foregoing ingredients are mixed in 500 ml. of distilled water. Heat may be applied as necessary to facilitate dissolution. This solution is applied to glass slides and allowed to evaporate at moderate temperatures (about 40° C.), producing a dry transparent surface. Cytological specimens placed on this surface are rapidly fixed and maintain all cellular characteristics and stain ability.

EXAMPLE 3

To the basic four component mixture described in Example 2 are added the following:

| Ingredient | Amount (% of mixture) |
| --- | --- |
| trichloroacetic acid | 12.8% (3.3 g.) |
| glyoxal | 0.4% (0.2 ml. of 40% solution) |

When all ingredients are thoroughly mixed, 1.6 g. of polyvinyl alcohol (Gelvatol 40/10) are added. The composition is utilized as in Example 2.

EXAMPLE 4

To the composition of Example 3 are added two drops (about 0.06 ml) of Triton 405 surfactant. This composition is heated to 40° C., applied to a sheet of poly(methyl methacrylate) [plexiglas] and dried at 40° C.

In addition to fixing histological, cytological and proteinaceous preparations, the precoted plastic slide becomes resistant to solvents such as xylene and toluene frequently encountered in slide preparation.

EXAMPLE 5

| Ingredient | Amount |
| --- | --- |
| 98% pyrrolid-2-one | 14.5 ml. |
| urea | 3.15 g. |
| polyethylene glycol (200 mw) | 10.5 ml. |
| zinc sulfate | 1.25 g. |

Seven milliliters of the pyrrolidone, 1.5 g. of the urea, 0.5 g. of the zinc acetate and 3.0 ml. of the polyethylene glycol are mixed with 500 ml. of distilled water.

To 100 ml. of this solution are added the following colloid protective composition:

| Dextrin (Kohdex) | 2 g. |
| --- | --- |
| Surfactant (Triton 405) | .005 mg. |
| Gelvatol G 20/60 | 4 g. |
| Acrylamide Formulation* | 6.7 ml. |

*prepared by dissolving 72 g. of acrylamide in 20 ml. of glycerol, 40 ml. of acetic acid and 75 ml. of acetone.

The remaining 7.5 ml. of pyrrolidone, 1.65 g. of urea, 0.75 g. of zinc acetate and 7.5 ml. of polyethylene glycol are mixed with 500 ml. of water and to this mixture are added 5 g. of Gelvatol G 20/60 and 0.025 mg. of Triton 405 surfactant.

Equal parts by weight of the first solution containing the protective colloid preparation and the second solution are combined with 16.7 parts by weight of milk latex coated β-UCG antigen. To slides of poly(methyl methacrylate) is applied 0.280 mg. of this mixture. The mixture is dried at 40° C. to leave an evaporative residue of the stabilized antigen which is stable at room temperature and will react with gonadotropic hormone antibody.

What is claimed is:

1. A diagnostic composition which comprises
   (a) a proteinaceous substance which is reactive in a diagnostic immunological reaction; and
   (b) as a principal active preservative component for said proteinaceous substance, a mixture of from about 10 to about 75% by weight of pyrrolid-2-one, from about 10 to about 50% by weight of polyol, from about 1 to about 20% by weight of a urea and from about 1 to about 10% by weight of a zinc salt of a nonoxidizing organic or inorganic acid, the relative percentages of said preservative component ingredients being selected from within the respective ranges so that their sum is 100% of said mixture.

2. A composition according to claim 1 wherein the proteinaceous substance is an antigen or antibody.

3. A composition according to claim 1 wherein the zinc salt is zinc acetate or zinc chloride.

4. A composition according to claim 1 wherein the pyrrolid-2-one constitutes from about 40 to about 60% by weight of said preservative component.

5. A composition according to claim 1 wherein said polyol is a polyethylene glycol which constitutes from about 20 to about 40% by weight of said preservative component.

6. A composition according to claim 1 wherein the urea constitutes of from about 5 to 15% by weight of said mixture.

7. A composition according to claim 1 wherein said pyrrolid-2-one constitutes from about 55 to about 60% of said preservative component, said polyol is polyethylene glycol having a molecular weight of about 200 and constitutes from about 20 to about 25% of said preservative component, said urea constitutes from about 10 to 15% of said preservative component and said zinc salt is zinc acetate and constitutes from about 3 to about 5% of said preservative component.

8. An aqueous formulation of a composition according to claim 1 comprising at least sufficient water to solubilize said mixture and suspend said proteinaceous substance.

9. A composition according to claim 1 wherein said proteinaceous substance is bound to a carrier.

10. A diagnostic test device comprising a base strip of material which is non-absorbent to and insoluble in water and carrying thereon at least one deposition area in which area is carried the evaporative residue of a diagnostic composition according to claim 1.

11. A device according to claim 10 wherein evaporative residues of different compositions are deposited in a single zone of said strip.

12. A device according to claim 10 wherein said strip is divided into a plurality of zones, each carrying the evaporative residue of the same or different diagnostic compositions.

13. A device according to claim 10 wherein said base strip is glass.

14. A device according to claim 10 wherein said proteinaceous substance is an antigen or antibody.

15. A device according to claim 10 wherein said base strip is plastic.

16. A device according to claim 15 wherein said plastic is polystyrene.

17. A device according to claim 15 wherein said plastic is a polyacrylate or polymethacrylate.

18. A device according to claim 15 wherein said plastic is polyvinyl chloride.

* * * * *